US006941795B2

(12) United States Patent
Maleville

(10) Patent No.: US 6,941,795 B2
(45) Date of Patent: Sep. 13, 2005

(54) METHOD FOR EVALUATING PARTICLE CONCENTRATIONS IN A CLEAN ROOM OR MACHINE MINI-ENVIRONMENT

(75) Inventor: Christophe Maleville, La Terasse (FR)

(73) Assignee: S.O.I. Tec Silicon on Insulator Technologies S.A., Bernin (FR)

( * ) Notice: Subject to any disclaimer, the term of this patent is extended or adjusted under 35 U.S.C. 154(b) by 87 days.

(21) Appl. No.: 10/664,782

(22) Filed: Sep. 16, 2003

(65) Prior Publication Data

US 2004/0069045 A1 Apr. 15, 2004

Related U.S. Application Data

(60) Provisional application No. 60/472,438, filed on May 22, 2003.

(30) Foreign Application Priority Data

Oct. 11, 2002 (EP) .............................. 02292518

(51) Int. Cl.$^7$ ............................................... G01N 37/00
(52) U.S. Cl. .................. 73/28.01; 73/28.01; 73/863.22; 73/865.5; 73/864.71
(58) Field of Search .......................... 73/863.22, 28.01, 73/865.5, 864.71

(56) References Cited

U.S. PATENT DOCUMENTS

| 3,498,110 A | * | 3/1970 | Hans .............................. 73/38 |
| 3,526,461 A | | 9/1970 | Lindahal et al. |
| 4,725,294 A | | 2/1988 | Berger |
| 5,804,494 A | | 9/1998 | Mitani et al. |
| 6,360,590 B1 | * | 3/2002 | Brown ......................... 73/104 |

* cited by examiner

Primary Examiner—Hezron Williams
Assistant Examiner—André K. Jackson
(74) Attorney, Agent, or Firm—Winston & Strawn LLP

(57) ABSTRACT

A method for evaluating particle concentrations in the atmosphere of a clean room or of a machine mini-environment is described. The method includes exposing a test surface of a test substrate to the atmosphere for a test time, capturing an amount of particles at the test surface of the substrate at the end of the test time, analyzing the amount of captured particles, and comparing the analyzed amount of particles with a reference amount of particles from a reference substrate. An evaluation of the atmosphere of the room or environment can thus be accomplished in a relatively short time.

20 Claims, 2 Drawing Sheets

METHOD FOR EVALUATING PARTICLE CONCENTRATIONS IN A CLEAN ROOM OR MACHINE MINI-ENVIRONMENT

CROSS-REFERENCE TO RELATED APPLICATION

This application claims the benefit of provisional application Ser. No. 60/472,438, filed May 22, 2003.

BACKGROUND ART

The present invention relates to a method for evaluating particle concentrations, such as surface contamination or atomic contamination and especially boron or phosphorus, in the atmosphere of a clean room or a machine mini-environment.

A clean room is a work area with controlled temperature, humidity and particle concentration to protect sensitive equipment or products from contamination. Many different organizations such as medical groups or integrated circuit manufacturers require facilities that include high quality clean rooms. These clean rooms are equipped with various expensive and complicated air supply cleaning systems that provide the rooms with dust-free filtered air. Nevertheless, in typical clean rooms used to manufacture semiconductor wafers, due to system leakage and inconsistent air filtering, a certain small amount of contaminants such as boron and phosphorus remains in or is added to the clean room atmosphere, and this can lead to contamination of the wafers. For example, boron or phosphorus contamination on a surface of a processed silicon wafer can amount to $10^{12}$ atoms per $cm^2$. These particles can diffuse into the silicon wafer surface during thermal treatment leading to a change of the dopant concentration in this region which affects the characteristic of the processed chips. Therefore, it is necessary to be aware of the particle concentration of the clean room.

Conventional technology used to monitor boron or phosphorus levels in a clean room environment operate by funneling room air through a liquid to form air bubbles, wherein part of the boron or phosphorus of the air bubbles dissolves in the liquid. After a relatively long period of time, which may be on the order of a day, the liquid picks up a large enough amount of boron or phosphorus that is adequate for analyzing. The boron or phosphorus content of the liquid is then evaluated, for example, by using a spectroscopy based analysis such as Atomic Spectroscopy or ICPMS.

This method is a relatively imprecise way to tell the real boron or phosphorus concentration of the air, because only an indefinite part of the actual boron or phosphorus content actually dissolves in the liquid. Most air samples containing boron or phosphorus escapes with the air bubbles from the liquid before dissolving. A further disadvantage is that this method takes a relatively long period of time to obtain results, and these results provide only a mean value of the boron or phosphorus of the clean room. Thus, improvements are needed in this area.

SUMMARY OF THE INVENTION

The invention relates to a method for evaluating particle concentrations in the atmosphere of a clean room or similar environment. The method includes exposing a test surface of a test substrate to the atmosphere for a test time to capture an amount of particles; analyzing the amount of captured particles; and comparing the analyzed amount of particles with a reference amount of particles from a reference substrate to determine the particle concentration in the environment.

Steps can be taken to enhance the accuracy of these measurements. Generally, at least the test surface of the test substrate is cleaned prior to exposing it to the atmosphere. If desired, the test surface that contains the captured particles can be bonded to a surface of a second substrate after the test time to avoid loss of captured particles prior to the analyzing step. The second substrate can be another test substrate, and the test pair of substrates can be separated before conducting the analyzing. This also can be achieved by abrading away at least one of the substrates.

In a preferred embodiment, the capturing of the particles is accomplished by annealing the test substrate. Generally, the annealing is performed for about 1 to about 3 hours at a temperature of between about 800° C. and about 1050° C. The analyzing of particle amounts preferably comprises evaluating an atomic concentration profile of the particles captured by the test substrate. This is generally accomplished by using a Secondary Ion Mass Spectroscopy (SIMS) device, and the atomic concentration profile is determined at the test surface of the test substrate. Specifically, the test surface can be analyzed over a thickness of about 100 to 500 nanometers.

It is also possible to produce a series of test substrates at predetermined intervals to periodically monitor the particle content of the environment. For example, a test substrate can be produced at intervals of about every 30 minutes so that the particle concentration in the room can be monitored continuously. The reference substrate can be periodically cleaned to provide an essentially particle-free reference for comparison purposes.

If desired, a reference surface of the reference substrate can be bonded with a second reference surface of a second reference substrate to form a reference substrate pair. The pair can be annealed to capture the particles, such and by annealing at an annealing temperature and for an annealing time that are essentially equal to those used for the test substrate. The particle concentration of the reference substrate can also be analyzed in the same manner as that used for the test substrate.

BRIEF DESCRIPTION OF THE DRAWING FIGURES

Embodiments according to the present invention will be described in the following detailed description with reference to the accompanying figures, in which.

DESCRIPTION OF THE PREFERRED EMBODIMENTS

Figure 1:
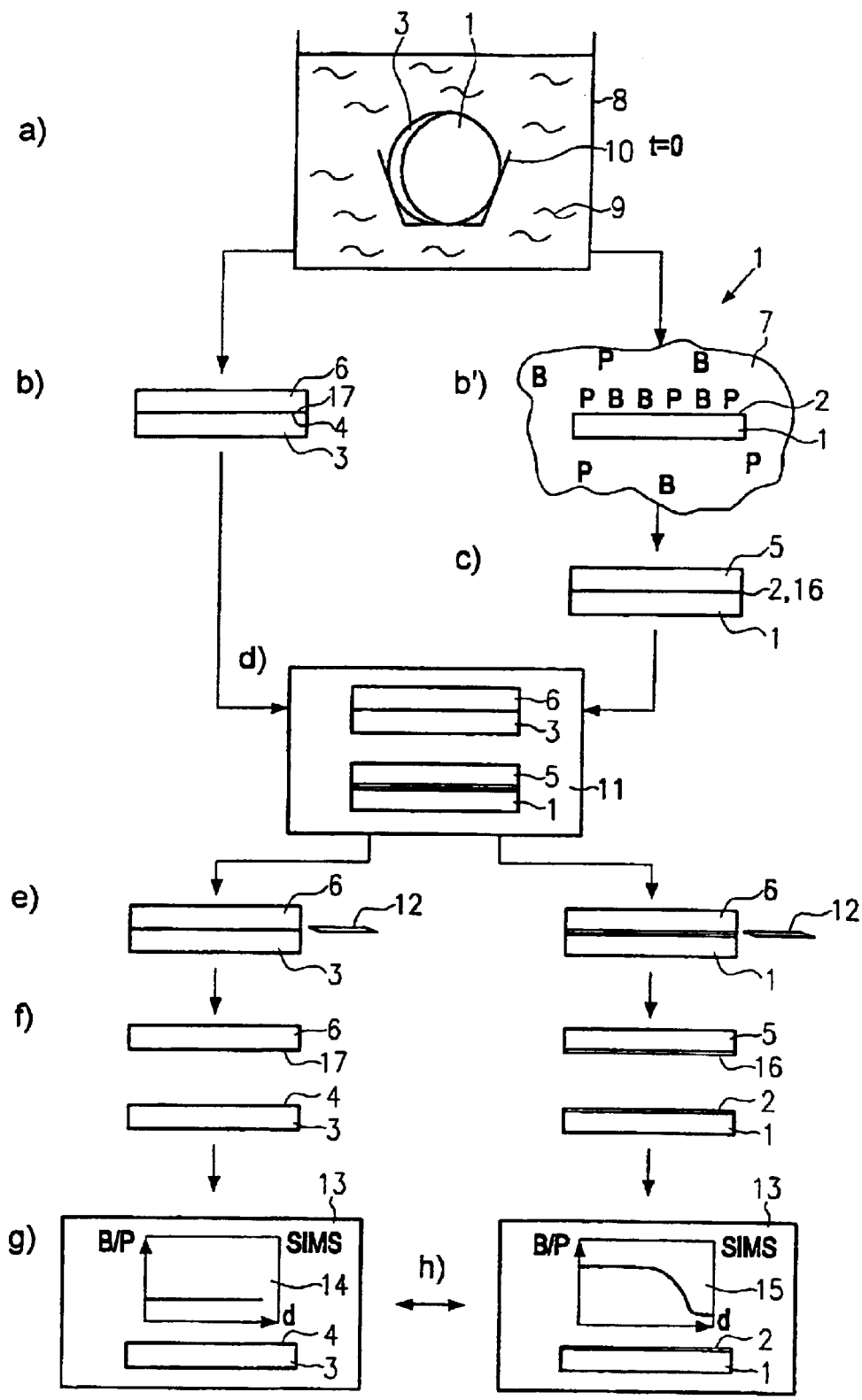
FIG. 1 shows an embodiment of the method for evaluating boron or phosphorus concentrations in an atmosphere of a clean room or a machine mini-environment according to the present invention.

The present invention provides a method for evaluating particle concentrations of the atmosphere in a clean room that takes a relatively short time to accomplish, and which reflects a more realistic and precise particle concentration of the clean room. The technique includes exposing a surface of a test substrate, especially of a silicon wafer, to the atmosphere for a test time. A particle amount is captured at the test substrate at the end of the test time, and this amount is analyzed and compared to a particle amount from a reference substrate.

The method permits a certain particle amount on the surface of the test substrate that closely corresponds to the actual particle concentration in the atmosphere of the clean room, to be captured at the test substrate after a definable test time for later analysis. This particle amount can represent the state of the test substrate during a certain time of contamination of the test substrate. A comparison between the analyzed particle concentration on the test wafer with that of the reference substrate then provides a relative particle concentration in the atmosphere of the clean room in the pre-defined time period. This allows the contamination of the atmosphere to be easily and conclusively determined.

The inventive method can be further used to monitor the particle concentration in similar environments, such as the mini-environment of a machine. Conveniently, the boron or phosphorus contamination of the test substrate may be caused for instance by filters in the machine mini-environment, ad this can be easily determined.

An advantageous embodiment of the invention further includes cleaning the test substrate before exposing it to the atmosphere. In this cleaning step, particles on the surface of the test substrate can be removed resulting in a nearly particle free test surface at the beginning of exposure of the test substrate to the atmosphere. Consequently, the analyzed particle amount directly corresponds to the particle concentration in the atmosphere from the beginning to the end of exposure of the test substrate to the atmosphere.

In a further advantageous embodiment, the step of capturing the particles includes joining or bonding the test surface of the test substrate with a surface of another or second substrate after the test time. The second substrate holds the particles which lay on, have been absorbed, or that have migrated into a region near the surface of the test substrate, to capture the particles in their actual position. This makes it possible to analyze the exact amount and determine the particle concentration in the atmosphere of the clean room. The second substrate can be of another material than the test substrate. In an advantageous example, the second substrate is another test substrate, which may be a silicon wafer, and the substrates form a test pair of substrates. Joining the test substrate to an equal or a similar substrate has the advantage that the substrates exhibit the same or comparable particle capture behavior. Furthermore, these substrates can easily be brought together to form, for instance, a bonded pair of substrates.

According to an advantageous variant of the invention, capturing the particles includes annealing the test substrate after the test time has ended. The annealing step permits captured particles to diffuse into the test substrate where they are conserved or fixed for further analysis. Annealing may be performed in a time range between about 1 to 3 hours, preferably for about 2 hours. The particles can thus diffuse into the test substrate creating a certain particle distribution which can be analyzed to evaluate the captured particle amount. An annealing time of 2 hours allows a particularly favorable penetration depth of the particles. The annealing may be performed at a temperature between 800° C. and 1050° C., preferably at 950° C. The diffusion activity of the particles is high enough at this temperature to obtain a good particle distribution in the test substrate which can be easily analyzed, and a good relationship between the created particle distribution and the required energy for diffusion is achieved at 950° C. The upper limitation of 1050° C. prevents an overly homogenous distribution of the particles in the substrate and/or an overly strong bonding of the substrates.

According to a specific embodiment of the invention, a test pair of substrates bonded to each other at the end of the test time are subsequently separated for analyzing. In this way, the test surface which was exposed to the atmosphere for the test time, and which state was fixed by the bonding step, is made accessible for analyzing the particle amount. In a further example, the method further includes an abrasion step, wherein at least one of the back sides of a test pair of substrates is abraded. The abrasion of material from a back side of the test pair of substrates may be conducted in a stepwise manner to reach the test surface, to analyze the particle amount at least at that surface. Analyzing the particle amount may include evaluating the atomic concentration profile of the test substrate. The atomic concentration profile gives a direct indication of a particle quantity included in and on the test substrate. The atomic concentration profile may be evaluated by a Secondary Ion Mass Spectroscopy device, which utilizes a very precise and efficient analyzing method to provide the atomic concentration profile of the test substrate. The atomic concentration profile can be evaluated at the test surface of the test substrate, and since the test surface is exposed to the atmosphere of the clean room, its atomic concentration profile closely reflects the particle concentration in the atmosphere.

In other preferable embodiments of the invention, the test surface is analyzed over a thickness of about 100 to 500 nanometers, preferably 200 nanometers. This thickness range gives adequate information about the particle amount in the test substrate. Analysis at the thickness of 200 nm allows an effective relationship between the expenditure of energy for analyzing the evaluated particle amount. According to another preferable variant, a series of test substrates is produced at predetermined time intervals, preferably about every 30 minutes. Such operation allows monitoring of the change of the particle concentration in the atmosphere of the clean room or the mini-environment over a given time period. In particular, time intervals of every 30 minutes permit a good overview of the particle concentration in the atmosphere of the clean room or the mini-environment. It is thus possible to evaluate a contamination rate in the clean room or the mini-environment.

Yet another preferable embodiment of the method includes cleaning the reference substrate, preferably together with the test substrate. The cleaned reference substrate represents a state without particles on the substrate at a time t=0 which can easily be compared with the test substrate. When the reference substrate is cleaned together with the test substrate, both substrates have the same starting conditions which improves the precision of the results of the comparison of the substrates.

In a further embodiment, a reference surface of the reference substrate is joined with a reference surface of another reference substrate. Thus, the initial or original condition on the reference surface of the reference substrate can be fixed for analyzing and obtaining reference values of an initial or original particle amount that can be compared with the particle amount of other test substrates. The method may also include annealing the reference substrate, so that a particle amount on the reference substrate can diffuse into the substrate to fix this particle amount in a region near the surface of the reference substrate. The annealing temperature and the annealing time of the reference substrate could be equal to an annealing temperature and an annealing time of the test substrate. Using the same annealing temperature and annealing time for both the test substrate and the reference substrate permits a better comparison of the measurement results. A particle amount of the reference substrate can be analyzed and then compared with the evaluated particle amount of the test substrate. The atomic concentration profile of the reference substrate can be analyzed to obtain the particle amount, and this atomic concentration profile can be compared with the test substrate. The atomic concentration profile of the reference substrate can be evaluated by Secondary Ion Mass Spectroscopy, which enables a precise evaluation of the particle amount in and on the reference substrate.

In a favorable embodiment, the atomic concentration profile of the reference substrate is evaluated at a reference surface of the reference substrate. This surface represents the initial or original particle amount on the reference substrate, which is a good indication of the particle amount on the reference substrate at the time t=0. This value can be compared with the particle amount analyzed on the test substrate. The reference surface of the reference substrate can be analyzed over a thickness of about 100 to 500 nanometers, preferably of about 200 nanometers. This thickness range corresponds to that for analyzing the test substrate and is therefore well suited for a further comparison between the reference substrate and the test substrate. The thickness of 200 nm allows particle analysis to be conducted of the relevant part near the surface of the substrate.

FIG. 1 shows an embodiment of the method for evaluating boron or phosphorus concentrations in an atmosphere of a clean room or a machine mini-environment. Silicon wafers 1, 3, 5 and 6 are shown being handled. N-type-silicon is used for a boron analysis, and p-type-silicon is used for phosphorus analysis. The substrate level $N_s$, which is the bulk dopant concentration of the silicon wafers, is lower than the level of the species which are to be analyzed.

Referring to FIG. 1a), two or more silicon wafers 1,3 are shown standing erect or inclined in a wafer holder 10. The wafers are submerged in a bath 8 containing a cleaning solution 9. The cleaning solution 9 removes inorganic and organic contaminants on surfaces 2,4 of the silicon wafers 1,3. The cleaning solution 9 may be a typical RCA cleaning solution, which can be complimented or replaced by other suitable solutions or mixtures of gases and solutions capable of removing any contaminants on the surfaces 2,4 of the silicon wafers 1,3. The cleaning solution 9 has a temperature between room temperature of about 19° C. to 25° C. and about 85° C., and can be stirred by a stirrer (not shown) or recirculated to obtain a homogenous concentration of the components of the cleaning solution.

In FIG. 1b), reference wafers 3 and 6 are bonded by bringing their surfaces together immediately after cleaning, and by covering or bonding the surfaces with each other. In FIG. 1b'), one of the cleaned silicon test wafers 1 and a another silicon test wafer 5 (not shown) are exposed to the atmosphere 7 of a clean room. The atmosphere 7 contains air which is contaminated with boron or phosphorus. A portion of the boron or phosphorus atoms are absorbed or deposited on the surface 2 of the silicon wafer 1.

In FIG. 1c), a bonded test wafer pair is formed between the test wafers 1 and 5. The test surface 2 of wafer 1 is bonded to the test surface 16 of wafer 5. The bonded reference wafer pair 3,6 includes an initial clean surface 4 as a reference at its bonding interface, whereas the test wafer pair 1,5 includes boron or phosphorus contaminants which have been deposited on the test surfaces 2,16 at the bonding interface of the test wafer pair.

In FIG. 1d), the bonded wafer pairs 3,6 and 1,5 are annealed in annealing equipment 11 at about 950° C. for approximately two hours. In this annealing step, at least the boron or phosphorus atoms trapped on the bonding interface between the test wafers 1 and 5 diffuse into the regions near the bonding interface of the wafers 1 and 5, and are thus captured.

In FIG. 1e), after annealing, the bonded wafer pairs 3,6 and 1,5 are separated with a razor blade 12 which is pushed between the bonded surfaces 4,17 and 2, 16. FIG. 1f) shows the wafers after separation. The boron or phosphorus content is increased in at least a region near the surfaces 2 and 16 of the wafers 1 and 5 due to diffusion of these particles into the silicon wafers 1 and 5.

In FIG. 1g), the atomic concentration profiles of the wafers 1 and 3 are analyzed using a Secondary Ion Mass Spectroscopy (SIMS) device 13. According to a profile 14, measured over about 200 nanometers of the surface beginning from the reference wafer 3, the boron or phosphorus concentration at the reference surface 4 of the reference wafer 3 is nearly constant. In contrast, in FIG. 1h), an atomic concentration profile 15 evaluated at the test surface 2 of the test surface 1 shows an increased concentration of boron or phosphorus, especially near the surface. The atomic concentration profiles 14 and 15 are compared with each other and a difference between the profiles is calculated. An integration of the profiles between the respective surface and bulk level results in a value of a deposited dose which is commonly expressed in atoms per $cm^2$. The calculated difference is a direct indication of the boron or phosphorus concentration of the atmosphere in the clean room because there is a direct proportional relationship between the boron or phosphorus content of the test wafer and the boron or phosphorus contamination of the atmosphere in the clean room.

Although the method shown with reference to FIGS. 1a) to 1h) pertains to silicon wafers, the method can also be applied to any substrates which are able to trap or capture particles in an atmosphere. Furthermore, the capture of particles can be attained in a single method step.

In the aforementioned described advantageous embodiment, the effect is realized by subsequent bonding and annealing steps. It is also contemplated that the substrate which is bonded to the test wafer can be a different material than the test wafer. Further, the wafers can be annealed at any temperature and for any annealing time that enables particles such as boron or phosphorus to be captured by the substrates being used. The annealing time and the resulting diffusion depth of the targeted species or particles depend upon the annealing temperature and the diffusion coefficients of the respective species. The analyzed depth "d" of the test wafer and of the reference wafer must be higher than the diffusion length of the analyzed particles or contaminants. A conventional SIMS-measurement for analyzing substrates can be replaced by a TOF-SIMS (Time-of-Flight-Secondary Ion Mass Spectroscopy) surface analysis.

The method has been described with reference to evaluating boron or phosphorus particle concentration in an atmosphere, but is should be understood that the method can also be applied to evaluate any other particle concentration or another type of contaminant in an atmosphere. Furthermore, instead of separating the wafers as shown in FIGS. 1e) and 1f), the captured particles can be made accessible for analysis by abrasion of one of the back sides of at least one of the wafers 1 or 5 shown in FIG. 1e). The region of interest can be approached by using a stepwise backwards abrasion of the material of at least one of these wafers, to reach one of the surfaces 2,16 that includes diffused particles for analysis.

Figure 2:
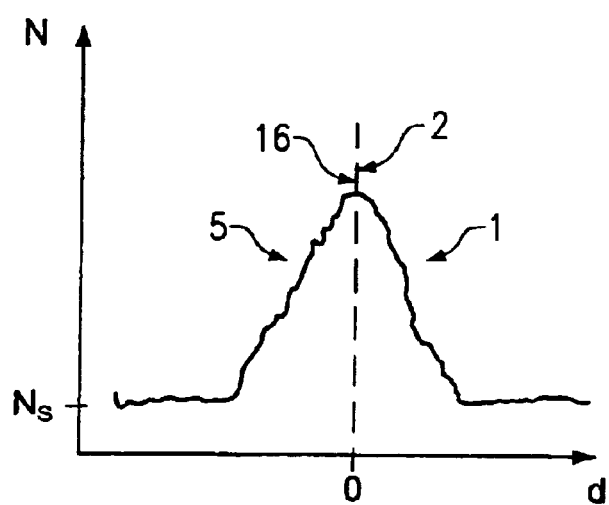
FIG. 2 is a graph of a concentration profile of a bonded test wafer pair.

FIG. 2 is a schematic diagram of a concentration profile of the bonded test wafer pair 1,5 after the annealing step. The concentration of diffused contaminants such as boron or phosphorus is shown as function of the depth. The depth d=0 corresponds to the respective surfaces 2 and 16 of the wafers 1 and 5.

Figure 3:
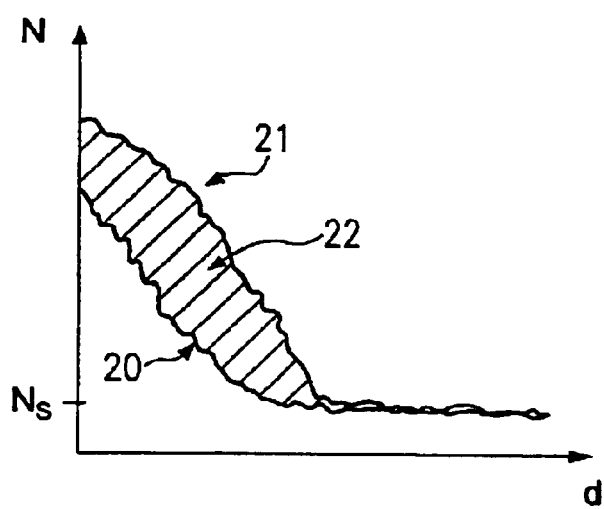
FIG. 3 is a graph of the SIMS-concentration profiles of a test wafer and a reference wafer.

FIG. 3 is a schematic diagram of a SIMS-concentration profile 21 of the test wafer 1 in comparison to a SIMS-concentration profile 20 of the reference wafer 3. The concentration of diffused contaminants is shown as a function of the analyzed depth d. The depth d=0 corresponds to the respective surfaces 2 and 4 of the wafers 1 and 3. The concentration of the targeted species, such as boron or phosphorus, near the surface of the test wafer 1 is higher than the concentration near the surface of the reference wafer 3. The difference 22 between the test profile 21 and the reference profile 20 is integrated to evaluate the surface dose of contaminants.

What is claimed is:

1. A method for evaluating particle concentrations in the atmosphere of a clean room or similar environment comprising:

exposing a test surface of a test substrate to the atmosphere for a test time to capture an amount of particles;

bonding the test surface that contains the captured particles to a surface of a second substrate after the test time to avoid loss of captured particles;

analyzing the amount of captured particles; and comparing the analyzed amount of particles with a reference amount of particles from a reference substrate to determine the particle concentration in the environment.

2. The method of claim 1 which further comprises cleaning at least the test surface of the test substrate prior to exposing it to the atmosphere.

3. The method of claim 1 wherein the second substrate is another test substrate.

4. The method of claim 3 which further comprises separating the test pair of substrates before conducting the analyzing.

5. The method of claim 1 which further comprises abrading away at least one of the substrates before conducting the analyzing.

6. A method for evaluating particle concentrations in the atmosphere of a clean room or similar environment comprising:

exposing a test surface of a test substrate to the atmosphere for a test time to capture an amount of particles;

analyzing the amount of captured particles; and comparing the analyzed amount of particles with a reference amount of particles from a reference substrate to determine the particle concentration in the environment;

wherein the capturing of the particles is accomplished by annealing the test substrate.

7. The method of claim 6 wherein the annealing is performed for about 1 to about 3 hours.

8. The me of claim 6 wherein the annealing is performed at a temperature of between about 800° C. and about 1050° C.

9. A method for evaluating particle concentrations in the atmosphere of a clean room or similar environment comprising:

exposing a test surface of a test substrate to the atmosphere for a test time to capture an amount of particles;

analyzing the amount of captured particles; and comparing the analyzed amount of particles with a reference amount of particles from a reference substrate to determine the particle concentration in the environment;

wherein the analyzing of particle amounts comprises evaluating an atomic concentration profile of the particles captured by the test substrate.

10. The method of claim 9 wherein the atomic concentration profile is determined by a Secondary Ion Mass Spectroscopy (SIMS) device.

11. The method of claim 9 wherein the atomic concentration profile is determined at the test surface of the test substrate.

12. The method of claim 11, wherein the test surface is analyzed over a thickness of about 100 to 500 nanometers.

13. The method of claim 1 which further comprises producing a series of test substrates at predetermined intervals to periodically monitor the particle content of the environment.

14. The method of claim 12 wherein a test substrate is produced at intervals of about every 30 minutes.

15. The method of claim 1 which further comprises cleaning the reference substrate to provide an essentially particle-free reference.

16. The method of claim 1 which further comprises bonding a reference surface of the reference substrate with a second reference surface of a second reference substrate to form a reference substrate pair.

17. The method of claim 16 which further comprises annealing the reference substrate pair.

18. The method of claim 17 wherein the reference substrate pair is annealed at an annealing temperature and for an annealing time that are essentially equal to those used for the test substrate.

19. The method of claim 1 which further comprises analyzing a particle concentration of the reference substrate.

20. The method of claim 19 wherein the analyzing of the particle concentration of the reference substrate is conducted in the same manner as that used for the test substrate.

* * * * *

UNITED STATES PATENT AND TRADEMARK OFFICE
CERTIFICATE OF CORRECTION

PATENT NO. : 6,941,795 B2
DATED : September 13, 2005
INVENTOR(S) : Maleville

It is certified that error appears in the above-identified patent and that said Letters Patent is hereby corrected as shown below:

Column 8,
Line 5, change "me" to -- method --.

Signed and Sealed this

First Day of November, 2005

JON W. DUDAS
*Director of the United States Patent and Trademark Office*